United States Patent [19]
Lai

[11] Patent Number: 6,011,061
[45] Date of Patent: Jan. 4, 2000

[54] THERAPEUTIC METHODS AND PREPARATIONS USING RUBIDIUM IONS

[76] Inventor: John Lai, 43 Eaglehawk Road, Bendigo, Australia

[21] Appl. No.: 08/875,950

[22] PCT Filed: Feb. 9, 1996

[86] PCT No.: PCT/AU96/00067

§ 371 Date: Aug. 8, 1997

§ 102(e) Date: Aug. 8, 1997

[87] PCT Pub. No.: WO96/24363

PCT Pub. Date: Aug. 15, 1996

[30] Foreign Application Priority Data

Feb. 10, 1995 [AU] Australia ........................................ 1048

[51] Int. Cl.⁷ ......................... A61K 33/00; A61K 33/14; A61K 9/70
[52] U.S. Cl. ......................... 514/492; 424/401; 424/402; 424/443; 424/445; 424/446; 424/447; 424/448; 424/449; 424/617
[58] Field of Search ................................. 424/401, 402, 424/443, 445, 446, 447, 448, 449, 617; 514/492

[56] References Cited

U.S. PATENT DOCUMENTS 5,254,583 10/1993 Ingomar et al. .......................... 514/492

FOREIGN PATENT DOCUMENTS

| 20464/88 | 2/1989 | Australia . |
| 55-69515 | 5/1980 | Japan . |
| WO 94/03189 | 2/1994 | WIPO .............................. A61K 33/14 |
| WO 94/11010 | 9/1994 | WIPO . |

OTHER PUBLICATIONS

Angelis et al, "Rubidium Chloride: Current Status of the Present Research", Drugs of Today, vol. 24, No. 10, pp. 733–741, 1988.

Chemical Abstract 89:157415, "Effect of Cesium, Lithium and Rubidium on Some Effects of Morphine", Dec. 1978.

Chemical Abstract 68:65591, "Mechanism of Adrenaline Formation Induced by Potassium, Rubidium and Cesium Ions", Nov. 1967.

Gennaro, Alfonso R., Ed., Remington's Pharmaceutical Sciences, 17th Edition, Mack Publishing, Easton, PA, 1985, pp. 1658–1659.

*Primary Examiner*—Frederick Krass
*Attorney, Agent, or Firm*—Christensen O'Connor Johnson & Kindness PLLC

[57] ABSTRACT

Various methods of treating the musculoskeletal, neural and respiratory disorders in a patient are disclosed wherein a preparation containing rubidium ions, preferably in the form of rubidium chloride, are administered externally and internally to the patient. In one preferred embodiment a topical preparation is provided, which consists of strips of microporous material on each side of a plastics backing layer impregnated with an aqueous solution containing rubidium chloride. In an alternative embodiment a cream preparation containing rubidium chloride is provided for external application to the patient.

23 Claims, 1 Drawing Sheet

THERAPEUTIC METHODS AND PREPARATIONS USING RUBIDIUM IONS

This patent application is a continuing application claiming foreign priority benefits. Specifically, this patent application claims the benefit of the filing date under 35 U.S.C. § 120 of International Application No. PCT/AU96/00067, filed Feb. 9, 1996, and also the benefit of the filing date under 35 U.S.C. § 119 of Australian Application Ser. No. PN1048, filed Feb. 10, 1995.

FIELD OF THE INVENTION

This invention relates to the treatment of a variety of distressing disorders that occur in both man and animals and to compositions and preparations for use in such treatment. As used herein, the term "patient" includes within its scope both humans and animals.

The invention finds particular application in the treatment of many seemingly unrelated complaints that cause huge health losses to individuals and huge financial losses to society. Some important applications of the present invention which have been noted to date include:

1) Relief of the pain in an extremely wide range of painful musculoskeletal and neural disorders.

2) The suppressing or relief of pain associated with respiratory disorders, such as of coughs as well as most of the symptoms of hayfever. This includes such important afflictions as asthma and the common cold, and croup attack in children.

BACKGROUND OF THE INVENTION

The current conventional Western medical practice for management of arthritis and other soft tissue injuries includes the administration of steroids and non-steroidal anti-inflammatory drugs by topical application, orally or by injection into the affected areas of the patient.

Steroids, such as the corticosteroids, often have undesirable side effects such as the promotion of peptic ulcers, increased susceptibility to infection, mental irritability, nervousness, obesity, muscular weakness, osteoporosis, diabetes, and adrenal insufficiency which, in some cases, may cause the patient to collapse.

Non-steroidal anti-inflammatory drugs generally have a less debilitating effect on patients. However, they are not without side effects. Stomach disorders, gastric pain, diarrhoea, dizziness or light headiness, stomach or duodenal ulcers and long term blood loss have all been reported in patients treated with non-steroidal anti-inflammatory drugs.

Where the ant-inflammatory drugs have been administered topically, further difficulties such as skin irritation, odor and staining may also be experienced.

Most commercially available topical preparations for the treatment of musculoskeletal disorders contain methyl salicylate as the active ingredient, but methyl salicylate is a toxic drug which can be lethal in large doses and it is possible that such large lethal doses may be attained by absorption through the skin.

The administration of gold has also been promoted in the management of arthritis. However, side effects have been reported in patients receiving gold administration including toxic hepatitis, renal failure, deafness, skin rashes and various blood disorders.

It is therefore desirable to provide a method of treatment of musculoskeletal and neural disorders which alleviates or ameliorates at least some of the difficulties associated with current treatment regimes.

Traditional Chinese remedies for the treatment of soft tissue injuries such as sprains and swellings, particularly of the ankles, include the packing of raw salt extracted from seawater around a painful or swollen joint. The application of the salt reduces the pain and swelling in many cases.

Further, acupuncturists postulate that there are three dimensional ribbon-like structures called meridians which are embedded in the body and join the acupuncture points. These meridians are postulated to be present in all mammals. It is postulated further that there is a flow of energy, possibly electromagnetic energy, flowing through these meridians and if, for any reason, this flow of energy is disrupted, disease will occur. By re-establishing the energy flow, the pain and inflammation which are often associated with neural and musculoskeletal injuries or disorders, and attributable to a disruption of the flow of energy through the meridians, can be reduced and thus aid in the eventual healing process.

DESCRIPTION OF PRIOR ART

My earlier International Patent Application No. PCT/AU93/00384 discloses an invention which involves the external application of caesium chloride in conjunction with other compounds which produce a synergistic effect in treating a wide variety of disorders in a patient, and the use of caesium chloride, either by itself or in conjunction with other compounds, in preparations for internal administration to a patient.

It has now been discovered that preparations containing rubidium ions, particularly but not exclusively in the form of rubidium chloride, can also be used effectively to treat musculoskeletal, neural and respiratory disorders, including those that are able to be treated with caesium chloride as described in my earlier patent application.

Various therapeutic uses of preparations containing rubidium ions have been previously proposed. A. K. Brewer, in an article entitled "The High pH Therapy for Cancer Tests on Mice and Humans" (Pharmacology Biochemistry & Behaviour, Vol. 21, Suppl. 1, pp. 1–5 1984), has disclosed that potassium, rubidium and especially caesium can be effective when administered internally to treat cancer. International Patent Application No. WO 94/11010 discloses that compositions of oak bark extract and synthetic mixtures containing potassium ions, zinc ions, calcium ions, rubidium ions and sulphur are useful in the treatment of skin cancer and other skin disorders. Australian Patent Application No. AU-B-20464 discloses a basic multielemental composition comprising a combination of several elements, including rubidium, and having useful therapeutic, dermatocosmetic and dietetic properties. However, none of these prior documents discloses the use of rubidium ions per se as a therapeutically active ingredient to treat musculoskeletal, neural or respiratory disorders.

SUMMARY OF THE INVENTION

According to a one aspect of the present invention, there is provided a method of relieving pain in a patient suffering from a musculoskeletal, neural or respiratory disorder which method comprises administering to said patient a preparation wherein the therapeutically active ingredient is rubidium ions. Preferably, the rubidium ions are in the form of rubidium chloride, RbCl.

It has been found that the external application of rubidium chloride reduces pain levels and swelling in swollen joints and has similar effects in the treatment of muscular disorders such as myositis.

The preparation containing rubidium chloride as the therapeutically active ingredient may be applied topically in the form of a gauze or other absorbent medium which has been impregnated with an aqueous solution containing rubidium chloride. The absorbent material may comprise any gauze or tissue, such as muslin tissue or self-adhesive tissue paper, but may conveniently comprise a microporous synthetic fabric material such as material sold by Minnesota Mining and Manufacturing Company under the Trade Mark "MICROPORE". The impregnated material is left to dry preferably at room temperature before being cut or otherwise severed into conveniently sized portions which may be attached to the appropriate part of the patient and secured in any convenient conventional manner.

According to another aspect of the invention there is provided a topical preparation for use in a method of treating musculoskeletal, neural or respiratory disorders in a patient wherein the preparation comprises an absorbent material impregnated with a therapeutically effective amount of rubidium ions, preferably in the form of rubidium chloride.

The rubidium chloride may be present in the absorbent material in a quantity of between about 0.01 mg/cm$^2$ to about 1.0 mg/cm$^2$, and preferably in a quantity of between about 0.1 mg/cm$^2$ to about 0.5 mg/cm$^2$.

DESCRIPTION OF THE PREFERRED EMBODIMENTS

EXAMPLE 1

Figure 1:
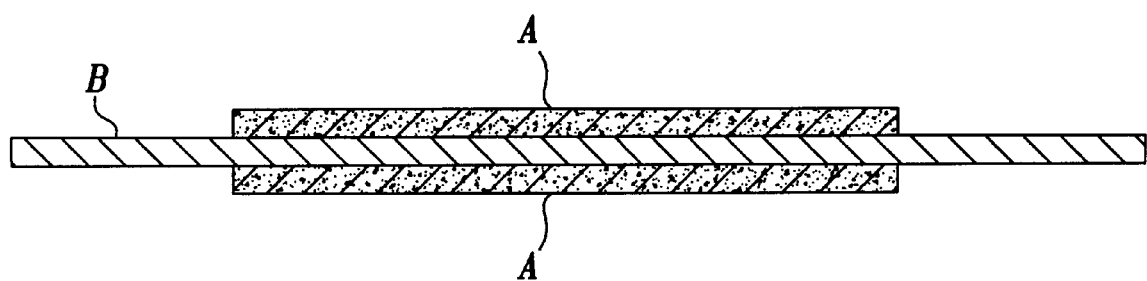
FIG. 1 illustrates a representative embodiment of the invention, a schematic section through a plastic strip having microporous material impregnated with rubidium chloride on both sides.

(1) One strip (A) of a self-adhesive microporous fabric material such as "MICROPORE" is applied on each side of a layer of plastic (B), hence the plastic layer (B) is sandwiched between the two layers (A) of the microporous material. The strip-like product then formed into a roll.

(2) The strip-like product is then immersed in an aqueous solution of rubidium chloride containing from about 0.1% to about 4%, preferably 2%, of rubidium chloride for about 8–12 hours, after which it is taken out of the solution and dried.

(3) The strip-like product can then be cut into patches of different sizes and the layers (A) of impregnated microporous material peeled off either side of the plastic strip (B) as required for application onto the skin of a patient.
AMOUNT OF RUBIDIUM CHLORIDE IN PATCHES OF THE STRIP 40 g of RbCl dissolved in two (2) litres of water can produce 20 rolls of a strip 7.5 cm wide and 9 m long. The total area of the strip is therefore 135000 cm$^2$ and contains 40 g of RbCl. Thus each cm$^2$ of the strip contains approximately 0.30 mg of RbCl.

Experiments and clinical observations have indicated that following the application of a microporous strip impregnated with rubidium chloride, test patients suffering from skeletal muscular pain caused by injuries, arthritis or other types of inflammation have experienced pain relief in a short period of time. The following are examples of clinical observations of the effectiveness of the preparation:

(1) A strip of absorbent material manufactured in the manner above was applied to the ball of the foot of a person who had been suffering from severe pain in the ball of the foot for two weeks. The patient found he could walk without much trouble within thirty minutes, and experienced no more pain after three days of treatment.

(2) A woman suffering from chronic back pain suffered many sleepless nights and had found no effective commercially available medication. After two strips of absorbent material impregnated with rubidium ions were applied to her back, she had her first good nights sleep for many years.

(3) A child had fallen and hurt his knee. The knee was swollen and painful, but an X-ray showed no fracture. One strip of absorbent material impregnated with rubidium ions was applied on each side of the knee. Two days later, all the pain and swelling had gone.

The concentration of rubidium chloride in the solution in which the absorbent material is impregnated may be as high as 50%, although it is believed there is not a great increase in the effectiveness when compared with a strip of absorbent material manufactured as described with reference to the example above.

Conversely, concentrations as low as 0.01% RbCl per litre of water have been shown to be effective although the time taken to achieve the desired reduction in pain and swelling levels is increased.

It will, however, be appreciated that the method of the present invention may be performed using different forms of preparations containing rubidium ions for external application to a patient. For instance, the method of the present invention in its broadest ambit includes the external application to a patient of therapeutically effective amounts of rubidium ions contained in creams, gels, pastes, lotions and sprays or the like, and even bath salts containing rubidium ions which may be added to baths, spa baths, mud baths etc. to provide a therapeutically effective amount of rubidium ions in the bath. It is also contemplated that, within the scope of the present invention, herbs or plants may be grown in rubidium enriched or fertilized soils or hydroponic solutions, with the plants being used to make preparations to be fed or administered internally or externally to a patient. Similarly, rubidium enriched clays containing therapeutically effective amounts of rubidium ions may be applied externally to a patient.

There is also provided, in accordance with a further aspect of the invention, a topical preparation for external application to a patient wherein the preparation comprises a cream, gel, paste, lotion, spray or the like containing a therapeutically effective amount or rubidium ions, preferably in the form of rubidium chloride.

The rubidium chloride may be incorporated into a cream base by conventional means known in the art. The rubidium chloride may be present in the preparation in an amount falling substantially within the range from about 0.1% to about 50% by weight. Preferably, the rubidium chloride is present in the cream in a quantity of between about 0.1% and about 4% of the total weight of the preparation.

An embodiment of this aspect of the invention will now be described in the following example.

EXAMPLE 2

300 g of rubidium chloride (RbCl) is mixed with 15 kg of an aqueous cream base, and then bottled in 50 ml jars.

Content of RbCl in the cream 300 g RbCl in 15 kg of cream

=20 g RbCl in 1 kg of cream

=20 mg RbCl in 1 g of cream (2%).

The cream may be applied by massaging gently into the affected areas. Suggested therapeutic amounts of rubidium chloride for external application to a patient are from about 0.001 mg to about 0.04 mg per cm$^2$ of the effected area of the patient. For example, 10 mg of cream containing about 2% of rubidium chloride may be applied over an area of skin of 10 cm$^2$ thereby administering approximately 0.02 mg of RbCl per cm$^2$ of skin.

Treatment with cream containing rubidium chloride can provide relief from arthritic pain in a short period of time. Preparations containing rubidium chloride have also been shown to provide beneficial effects when used in conjunction with orthodox methods of treatment, for example, physiotherapy or acupuncture.

Apart from the treatment of musculoskeletal disorders including rheumatic or arthritic disorders, the external application of preparations containing rubidium ions to patients having painful varicose veins, and neural disorders such as, migraines or other severe headaches, toothache, ear ache, period pains and stomach pains, has been demonstrated to provide significant relief in pain levels experienced by the patient.

A further beneficial application of preparations containing rubidium ions, preferably rubidium chloride, whether alone or in conjunction with other compounds, is the application of the preparation internally or externally to relieve coughing, a blocked or runny nose, or other symptoms in a patient suffering from a respiratory disorder.

Thus, according to another broad aspect of the invention there is provided a method of treating disorders of the respiratory system of a patient, which method comprises administering to said patient a preparation containing rubidium ions, preferably rubidium chloride.

This method of treatment finds particular application in the relief of coughing and chest congestion, relief from croup attack in children, as well as relief of the symptoms of hayfever. It will, however, be appreciated that the invention is not limited thereto and the treatment of patients having other symptoms of respiratory disorders such as blocked or runny noses or other symptoms of asthma, common colds and influenza falls within the ambit of the present invention.

In treating respiratory disorders the rubidium ions may be administered either externally or internally to the patient.

The rubidium ions may be administered externally by applying a topical preparation, for instance a cream, paste, lotion, spray or the like containing rubidium chloride, to the chest, throat, nasal area or other part of the body of the patient. The present invention therefore includes within its ambit a topical preparation for use in the treatment of respiratory disorders, wherein the preparation contains a therapeutically effective amount of rubidium ions preferably in the form of rubidium chloride.

The preparation is preferably applied topically in the form of a cream containing rubidium chloride.

The rubidium chloride may be incorporated into a cream base by conventional means known in the art. The cream preparation described above for use in the treatment of musculoskeletal and neural disorders has been found to be equally effective in relieving coughing and congestion in patients suffering from respiratory disorders. As described above, the rubidium chloride is preferably present in the cream in a quantity of between about 0.1% and about 4% of the total weight of the preparation.

The cream may be applied by massaging gently into the affected area, such as the chest or throat and has been shown to provide positive suppression of coughing within minutes after application. The cream can also provide relief of most symptoms of hayfever by applying it around the nasal area.

It has also been found that rubidium ions, preferably in the form of rubidium chloride, administered internally to a patient also have beneficial effects in suppressing or relieving any type of cough, as well as relieving most symptoms of hayfever. The rubidium ions may be administered internally in any convenient form, for instance, an aqueous solution of rubidium chloride could be used in a nebulizer, in an aerosol inhaler, in a nasal spray, as a mouth wash or administered with a dropper. Additionally, rubidium chloride could be added to a liquid or syrup to produce a cough mixture. Thus, the present invention also includes within its ambit a preparation for internal administration to a patient for treating coughs, respiratory disorders or hayfever, wherein the preparation comprises a carrier and, as the therapeutically active ingredient, rubidium ions.

In a preferred embodiment of this aspect of the invention the preparation comprises an aqueous solution of rubidium chloride. The aqueous solution may contain from about 0.01% to about 50% of rubidium chloride and preferably contains between about 0.2% and about 4% of rubidium chloride. Such a solution is preferably placed within a nebulizer or aerosol inhaler for administration to a patient who then can inhale a dose of rubidium chloride from about 0.08 mg to about 1.6 mg from the nebulizer or aerosol inhaler as described with reference to the following example.

EXAMPLE 3

An amount of rubidium chloride (RbCl) is dissolved in distilled water to produce an aqueous solution containing about 2% rubidium chloride, 2 ml of which is then placed in a nebulizer or aerosol inhaler.

2 ml of a 1% solution contains 0.04 g RbCl. 2 ml is a sufficient quantity for about 50 inhalations or "puffs". Thus each puff or inhalation from the nebulizer or inhaler contains 0.8 mg of RbCl.

Inhalations containing rubidium chloride have been found to suppress coughs within a matter of a few minutes, and such inhalations have also been found to suppress and relieve symptoms of hayfever. No significantly adverse effects have been noticed in patients that have repeatedly inhaled doses of rubidium chloride from a nebulizer or aerosol inhaler.

Rubidium chloride appears to be a selective blocker for local nerve endings. In this case, it blocks the transmission of a signal that would result in a cough. It also appears to have an anti-histamine like property, since it can suppress the symptoms of hayfever, although the actual mechanism is not clear. It also has a bronchodilatory effect, which is more powerful than the most commonly used bronchial dilator SALBUTAMOL (VENTOLIN).

Coughs due to colds cause extreme distress to typical northern hemisphere wintertime residents. Any treatment that would reduce the drain of energy and health in the course of the cold would certainly help in recovery from the common cold.

Croup attack in children can be a terrifying experience to a child too young to be able to understand the explanations made by adults. The incessant nature of this complaint can easily cause more pain and suffering to the parents than to the child. However, cream containing rubidium chloride can rapidly bring relief to both the child and indirectly to the parents.

It is desirable to state that many different kinds of cough can be suppressed because it is postulated that the rubidium chloride is selectively blocking the nerves rather than responding to a specific affliction that produces that cough. Here the intrinsic healing capabilities of the body are potentiated by removal of the antagonism caused by coughing.

From the above description, it will be appreciated that the methods and preparations of the present invention is effective in relieving pain caused by musculoskeletal and neural disorders, in suppressing coughs and in treating or relieving pain in other respiratory disorders. Preparations containing rubidium ions, for instance in the form of rubidium chloride have also been found to be effective in treating inflammation of epithelial tissue such as lining of respiratory system and gastrointestinal system.

The present invention has also identified that preparations including rubidium ions, preferably rubidium chloride, can be administered internally for various therapeutic treatments, particularly for treating respiratory and bronchial disorders, and also as a local anaesthetic. It will also be appreciated that various modifications and alterations may be made to the methods and preparations described above without departing from the scope and spirit of the present invention.

What is claimed is:

1. A method of treating or relieving pain in a patient suffering from a musculoskeletal or respiratory disorder, which method comprises administering to said patient a preparation in which the therapeutically active ingredient is rubidium ions.

2. A method according to claim 1 wherein the preparation is administered externally to the patient.

3. A method according to claim 1 wherein the rubidium ions are present in the form of rubidium chloride.

4. A method according to claim 2 wherein the preparation is administered topically in the form of an absorbent material impregnated with an aqueous solution containing rubidium ions.

5. A method according to claim 4 wherein an absorbent material containing an amount of rubidium chloride falling within the range from about 0.01 to about 1.0 mg/cm$^2$ is applied to the patient.

6. A method according to claim 4 wherein an absorbent material containing an amount of rubidium chloride falling within the range from about 0.1 to about 0.5 mg/cm$^2$ is applied externally to the patient.

7. A method according to claim 4 wherein an absorbent material containing rubidium in an amount of approximately 0.3 mg/cm$^2$ is applied externally to the patient.

8. A method according to claim 2 wherein the preparation is administered topically in a form selected from the group consisting of a cream, gel, paste, lotion, and spray containing a therapeutically effective amount of rubidium ions.

9. A method according to claim 8 wherein the rubidium ions are present in the form of rubidium chloride.

10. A method according to claim 9 wherein the preparation contains an amount of rubidium chloride falling within the range from about 0.01% to about 50% by weight.

11. A method according to claim 10 wherein the preparation contains an amount of rubidium chloride falling within the range from about 0.1% to about 4% by weight.

12. A method according to claim 10 wherein the preparation contains an amount of approximately 2% by weight of rubidium chloride.

13. A method according to claim 2 wherein the preparation is administered to the patient by applying doses containing an amount of rubidium chloride falling within the range from about 0.0001 to about 0.04 mg/cm$^2$ to the affected area of the patient.

14. A method according to claim 2 wherein the preparation is administered in the form of a bath salt containing rubidium ions.

15. A method of treating or relieving pain in a patient suffering from a respiratory disorder wherein a preparation containing rubidium ions as the therapeutically active ingredient is administered internally to the patient.

16. A method according to claim 15 wherein the preparation is administered to the patient in the form of a liquid, syrup or aqueous solution containing rubidium ions.

17. A method according to claim 16 wherein the preparation is administered to the patient in the form of a nebulizer, aerosol inhaler or spray containing an aqueous solution of rubidium ions.

18. A method according to claim 15 wherein the rubidium ions are present in the form of rubidium chloride.

19. A method according to claim 18 wherein an aqueous solution containing an amount of rubidium chloride falling within the range from about 0.01% to about 50% is administered to the patient.

20. A method according to claim 19 wherein an aqueous solution containing an amount of rubidium chloride falling within the range from about 0.2% to about 4% is administered to the patient.

21. A method according to claim 16 wherein an aqueous solution containing approximately 2% of rubidium chloride is administered to the patient.

22. A method according to claim 16 wherein the preparation is administered to the patient in doses containing an amount of rubidium chloride falling within the range from about 0.08 mg to about 1.6 mg.

23. A method according to claim 16 wherein the preparation is administered to the patient in doses containing an amount of rubidium chloride of approximately 0.8 mg.

* * * * *